United States Patent [19]

Yock et al.

[11] Patent Number: 5,029,588
[45] Date of Patent: Jul. 9, 1991

[54] LASER CATHETER WITH IMAGING CAPABILITY

[75] Inventors: Paul G. Yock, San Francisco; James W. Arenson, Woodside, both of Calif.

[73] Assignee: Cardiovascular Imaging Systems, Inc., Sunnyvale, Calif.

[21] Appl. No.: 366,906

[22] Filed: Jun. 15, 1989

[51] Int. Cl.$^5$ .............................................. A61B 8/00
[52] U.S. Cl. ........................... 128/662.06; 128/660.03; 606/7; 606/18
[58] Field of Search ....................... 128/660.03, 662.06

[56] References Cited

U.S. PATENT DOCUMENTS

| | | | |
|---|---|---|---|
| 3,938,502 | 2/1976 | Bom | 128/662.06 |
| 4,418,688 | 12/1983 | Loeb | 128/6 |
| 4,445,892 | 5/1984 | Hussein et al. | 604/101 |
| 4,576,177 | 3/1986 | Webster, Jr. | 128/660.03 |
| 4,587,972 | 5/1986 | Morantte, Jr. | 128/660.03 |
| 4,686,979 | 8/1987 | Gruen et al. | 128/303.1 |
| 4,794,931 | 1/1989 | Yock | 128/660.03 |
| 4,821,731 | 4/1989 | Martinelli et al. | 128/600.03 X |
| 4,887,605 | 12/1989 | Angelsen et al. | 128/660.03 |

FOREIGN PATENT DOCUMENTS 0163502 12/1985 European Pat. Off. .
7814494 11/1979 France .
WO83/01893 6/1983 PCT Int'l Appl. .

*Primary Examiner*—Francis Jaworski
*Attorney, Agent, or Firm*—Townsend and Townsend

[57] ABSTRACT

Vascular catheters include ultrasonic imaging capability and optical waveguides for delivering laser energy for ablating vascular obstructions. The ultrasonic imaging capability comprises a fixed ultrasonic transducer which directs ultrasonic energy at a reflective surface on a rotating element. The rotating element allows the interior of the blood vessel to be scanned prior to the application of laser energy to ablate the obstruction.

4 Claims, 2 Drawing Sheets

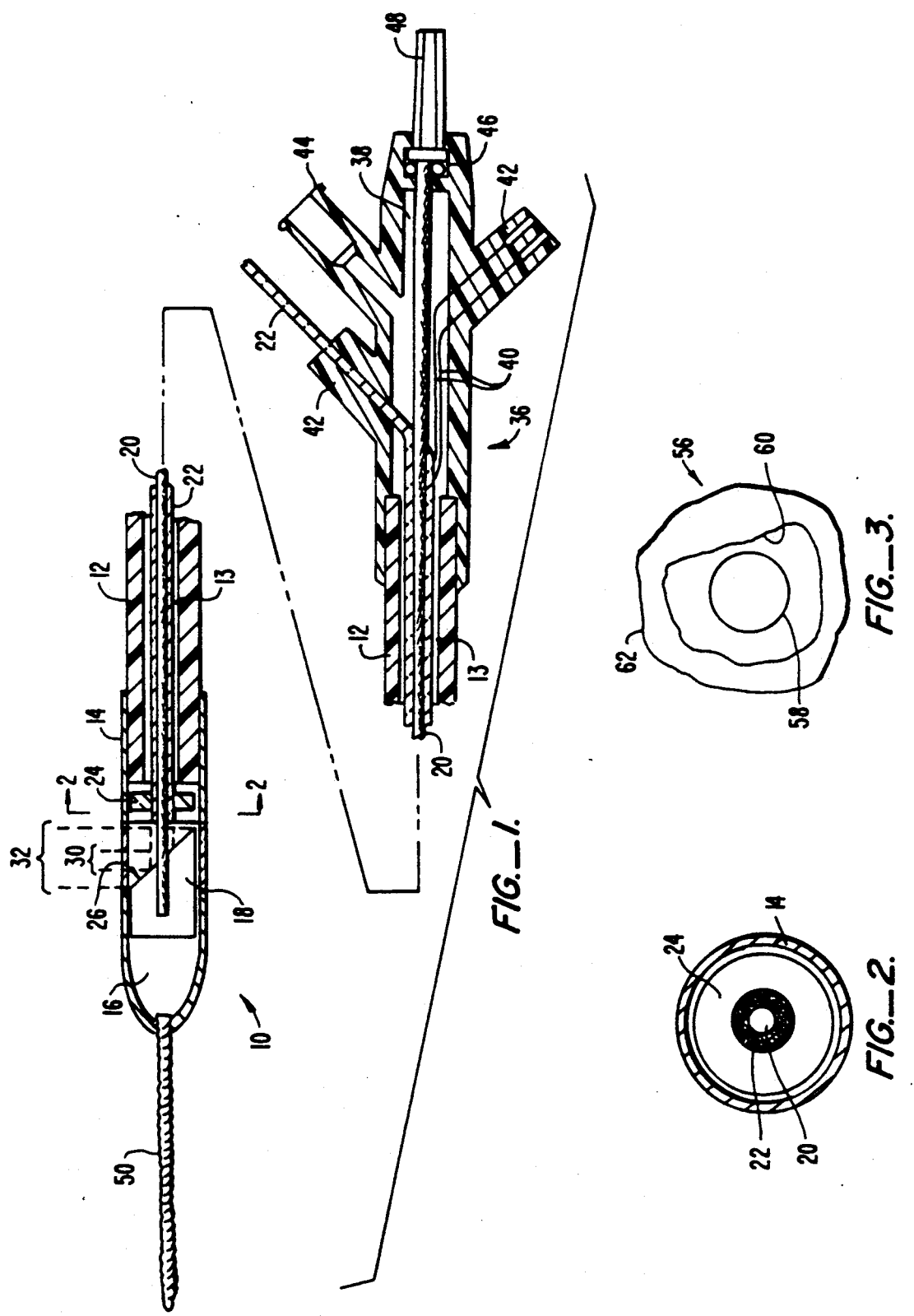

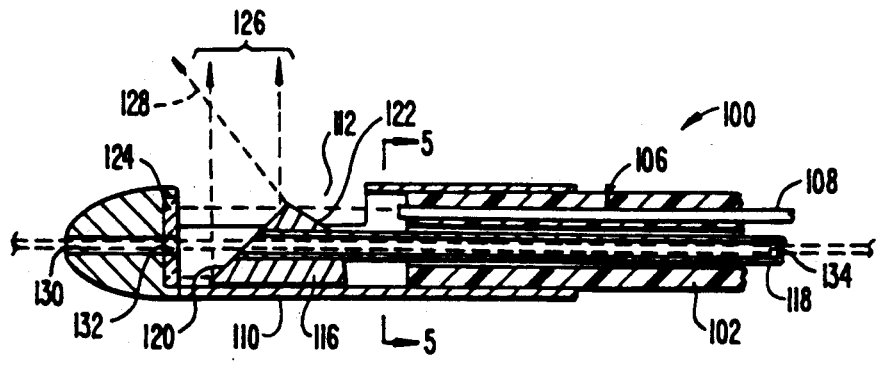
FIG._4.
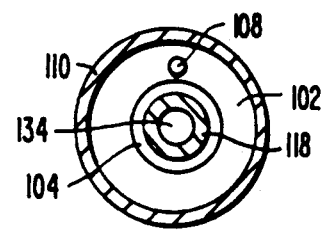
FIG._5.
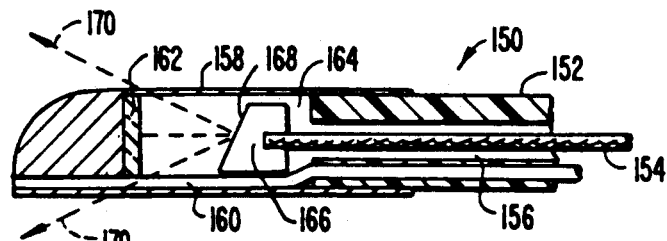
FIG._6.
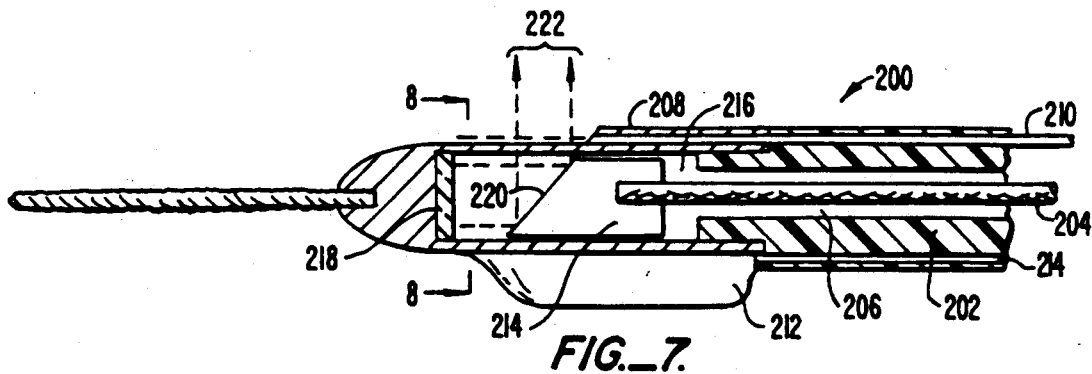
FIG._7.
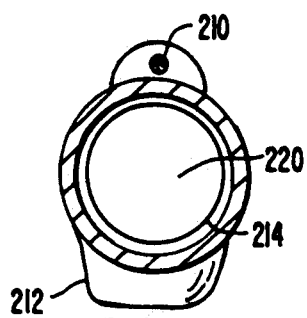
FIG._8.
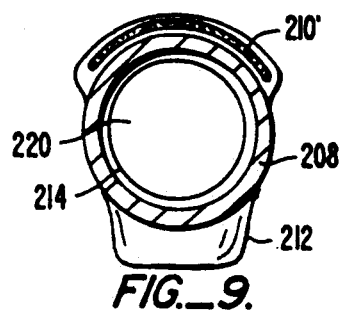
FIG._9.

LASER CATHETER WITH IMAGING CAPABILITY

BACKGROUND OF THE INVENTION

1. Field of the Invention

The present invention relates generally to the construction and use of vascular catheters. More particularly, the present invention relates to a vascular catheter which provides both ultrasonic imaging capability and an optical system for delivering laser energy within the field of view of the imaging capability.

Arteriosclerosis is a pandemic health problem which can cause myocardial infarction (heart attack) and a variety of other circulatory diseases. Arteriosclerosis is characterized by vascular constrictions, generally referred to as stenoses, which result from the formation of atheroma on the interior wall of the blood vessel. Initially, atheroma is soft and has a relatively low density. Over time, however, the atheroma calcifies into a hard plaque having a high density which can significantly occlude a blood vessel. Moreover, once plaque forms, platelets can aggregate on the diseased blood vessel wall, further occluding the lumen.

Numerous approaches for reducing and removing such vascular obstructions have been proposed, including balloon angioplasty where a balloon-tipped catheter is used to dilate a region of stenosis, atherectomy where a blade or cutting bit is used to sever and remove the obstruction, and laser angioplasty where laser energy is used to ablate at least a portion of the obstruction.

Each of these approaches finds use under different circumstances. For example, laser angioplasty is well suited for penetrating severe occlusions which leave little or no room for entry of balloon or atherectomy catheters. By utilizing appropriate wavelengths, laser energy can be used to penetrate even the most refractory stenoses. Frequently, laser angioplasty is utilized to create a passage through a severe occlusion, and the resulting passage utilized for subsequent balloon angioplasty or blade atherectomy to debulk or widen the lumen. Laser angioplasty is advantageous in that it generally results in the ablation of the occluding material, minimizing the release of emboli and other particulates which can cause secondary circulatory problems.

Despite its advantages, laser angioplasty suffers from numerous drawbacks. In particular, because of the high penetrating power, misdirection of the laser beam can cause penetration and piercing of the blood vessel wall. This problem arises because of the difficulty in positioning and aiming a laser catheter within a blood vessel. Generally, such positioning and aiming is accomplished by fluoroscopy which yields little information concerning the position of the cell wall, the precise direction in which the laser is aimed, and the nature of the obstructing material. The latter information is important because hardened plaque will generally require more energy to penetrate than relatively soft plaque or thrombus.

To overcome these problems, it has been proposed to combine laser angioplasty with various viewing systems. Most commonly, laser catheters have been provided with optical viewing systems employing optical waveguides which run in parallel with the waveguides carrying the laser energy. Such systems, however, are problematic in that they require stoppage of blood flow and flushing of the blood vessel with a clear liquid such as saline in order to allow viewing. Moreover, optical systems provide little or no information concerning the amount and distribution of plaque in the arterial wall.

To partially overcome these limitations, the use of ultrasonic imaging sensors with laser catheters has been proposed. In particular, a fixed ultrasonic transducer has been placed at the distal end of a catheter tube with an optical waveguide terminating at its center. The optical waveguide is coupled to a laser energy source and generally directs laser energy in the direction of viewing. The system, however, is limited to generally forward viewing and laser ablation, and is not particularly useful in debulking or widening the arterial lumen.

In addition to aiming difficulties, laser catheters generally have a very narrow field of penetration and have not been particularly useful in widening blockages in the blood vessel lumen. While some provisions have been made for deflecting a laser beam laterally to remove plaque and thrombus from the blood vessel wall, without precise information on the thickness of the stenosis, the chance of piercing the blood vessel is greatly increased.

For these reasons, it would be desirable to provide laser catheters having improved imaging capability. In particular, it would be desirable to provide laser catheters having an ultrasonic imaging capability which can be used to scan a relatively wide path around the blood vessel wall. Such systems should allow for precise aiming and control of the laser energy in order to provide for maximum penetration and ablation without damaging the blood vessel wall. Such systems should be useful for widening the central lumen in a radial direction as well as penetrating the lumen axially.

2. Description of the Background Art

Vascular catheters carrying fiber optics waveguides to deliver laser energy to stenosed regions within a blood vessel are known. U.S. Pat. No. 4,686,979, discloses a waveguide which is coupled to an excimer laser for performing laser angioplasty. U.S. Pat. No. 4,418,688, discloses a catheter having a waveguide carrying fiber optics for both viewing and delivery of laser energy, where the distal tip of the waveguide is deflectable to allow selective direction of the laser energy. WO 83/01893 (PCT US82/01669) also describes a vascular catheter which carries fiber optics for both viewing and laser ablation. U.S. Pat. No. 4,445,892, describes a vascular catheter having a rotatable axial waveguide with a mirror or prism at its end for allowing transverse viewing and transverse deflection of laser energy. U.S. Pat. No. 4,576,177, describes a vascular catheter including an optical fiber for delivering laser energy and a fixed ultrasonic transducer at the forward end for imaging an obstruction. A lens at the forward end of the optical fiber aligns the laser energy with the viewing direction of the transducer. U.S. Pat. No. 4,587,972 discloses a vascular catheter having a fiber optic bundle extending its length. A piezoelectric coating on the fibers at their distal end can generate axially directed ultrasonic energy in order to produce a longitudinal cross-sectional image. U.S. Pat. No. 3,938,502, describes an esophageal catheter having a plurality of radially-spaced ultrasonic transducers at its distal end. The transducers are utilized to obtain a complete cross-sectional view of the organ surrounding the catheter. French Patent Publication No. 78-14494 describes an esophageal catheter having an ultrasonic catheter rotatably mounted in a balloon. The transducer may be turned to direct the ultrasonic energy in a desired direction. European patent application 163 502 describes an atherectomy device using an axially translatable, rotating blade.

U.S. Pat. No. 4,794,931 and copending application Ser. No. 07/290,533, each describe a vascular catheter which combines an ultrasonic imaging capability with an atherectomy blade for severing stenosis from the vascular wall. The entire disclosures of both the patent and the application is incorporated herein by reference.

SUMMARY OF THE INVENTION

According to the present invention, vascular catheters are provided with both optical waveguides for delivering laser energy to a region of vascular stenosis and ultrasonic transducers for imaging the interior of the blood vessel proximate the region of stenosis. The ultrasonic transducer is positioned at a distal end of a flexible catheter tube and directs laser energy toward a reflective surface on a rotatable member within said distal end. A mechanism for rotating the rotatable member, typically a cable extending through a central lumen of the flexible catheter tube connected to a motor, is used to radially scan the ultrasonic energy across a desired location on the interior of the blood vessel. Manual scanning of the rotatable member will also be possible, but generally less desirable. Optionally, the rotatable member can be axially advanced or retracted within the catheter, allowing further positioning of the ultrasonic beam. By scanning the interior of the blood vessel, a profile of the stenosis can be obtained which is useful in directing the laser energy at an appropriate location to ablate stenosis without penetrating or damaging the wall of the blood vessel.

In a first embodiment, a single reflective surface is provided on the rotatable member to synchronously reflect both the ultrasonic scanning beam and the laser energy in a substantially transverse direction. Conveniently, the ultrasonic and laser beams will be coaxial in order to assure precise tracking of the observed image and the aim of the laser radiation. The rotatable member is first used to scan an annular profile of the blood vessel, determining the varying thickness of the stenosis and the position of the blood vessel wall. The laser beam can then be precisely directed at a characterized region of the stenosis at an intensity and for a length of time determined to be sufficient to remove the stenosis without damaging the blood vessel wall. Typically, the laser will be fired in controlled pulses or bursts in order to incrementally ablate the stenosis, allowing progress to be monitored by the imaging capability. The first embodiment is particularly advantageous in allowing precise control and removal of stenosis, allowing widening of the vessel lumen and debulking.

In a second embodiment of the present invention, the rotatable member includes separate reflective surfaces for the laser beam and the ultrasonic scanning beam. The provision of separate surfaces allows non-parallel direction of the laser beam and ultrasonic beam, and generally simplifies the construction of the catheter. Usually, the laser beam and ultrasonic scanning beam will be oriented to intersect at a location just outside the periphery of the catheter, and the advantages of the system will be the same as with the first embodiment.

In a third embodiment, a single reflective surface is used to project a forward, conical ultrasonic scanning beam. The laser waveguide is positioned to project a beam generally forward of the catheter, and the imaging information is used to assure that the laser beam is directed centrally through the blood vessel lumen. This embodiment is particularly useful for penetrating severe blockages in order to widen the lumen sufficiently to accommodate other types of catheters. The conical imaging allows precise alignment of the laser beam, greatly reducing any risk of penetration of the blood vessel wall.

In a fourth embodiment, a single reflective surface is provided for radially scanning the interior surface of the blood vessel. The optical waveguide terminates along the periphery of the catheter at a location spaced proximally from the distal end thereof. Generally, the waveguide will terminate just to the rear of the radial scan pattern provided by the reflective surface, so that laser radiation directed by the waveguide will penetrate a region which is scanned. This embodiment is particularly suited for incremental removal of stenosis. By providing a low power or controllable power laser beam, penetration of the laser energy can be limited to a thin layer or region adjacent the periphery of the catheter within the view of the scanning ultrasonic beam. The waveguide can be a small bundle of optical fibers capable of delivering a narrow beam of laser energy, or will preferably be a wide crescent-shaped band of optical fibers to provide for the shaving of annular layers of stenosis.

BRIEF DESCRIPTION OF THE DRAWINGS

FIG. 1 is a sectional view of a first embodiment of a catheter constructed in accordance with the principles of the present invention.

FIG. 2 is a cross-sectional view taken along line 2—2 of FIG. 1.

FIG. 3 illustrates a cross-sectional image provided by the ultrasonic scanning system of the catheter of FIG. 1.

FIG. 4 is a second embodiment of a catheter constructed in accordance with the principles of the present invention.

FIG. 5 is a cross-sectional view taken along line 5—5 of FIG. 4.

FIG. 6 is a third embodiment of a catheter constructed in accordance with the principles of the present invention.

FIG. 7 is a fourth embodiment of a catheter constructed in accordance with the principles of the present invention.

FIG. 8 is a cross-sectional view taken along line 8—8 of FIG. 7.

FIG. 9 is a cross-sectional view similar to FIG. 8, but illustrating an alternate embodiment of the fiber optic bundle of the optical waveguide of the catheter of FIG. 7.

DESCRIPTION OF THE SPECIFIC EMBODIMENTS

The present invention provides unique catheter constructions and methods for use in laser ablation angioplasty. By providing ultrasonic imaging capability in catheters having optical waveguides, laser energy can be specifically directed to desired portions of vascular obstructions in order to remove or lessen such obstructions without damage to the surrounding blood vessel wall.

Ultrasonic imaging capability is provided by an ultrasonic transducer, such as a piezoelectric crystal oscillator, located at the distal end of a flexible catheter tube, as described in more detail hereinafter. The piezoelectric crystal should be capable of operating at a frequency in the range from about 5 to 50 MHz and is typically formed from a crystalline material, such as barrium titanate, cinnabar, or zirconate-titanate. The crystal will be formed into a flat plate having suitable dimensions to fit within the distal end of the flexible catheter tube. The thickness of the plate will generally be chosen to provide the desired operational frequency. The opposed surfaces of the crystalline plate will be covered by metallic conducting films formed from a suitable material, such as chrome or gold. The material can be applied to the crystalline foil or can be evaporated or sputtered onto the opposite surfaces of the crystal. The resulting films serve as electrodes and are connected to wire leads by a suitable means, such as solder. Usually, the crystal will be mounted on a relatively large mass within the distal end of the catheter in order to provide suitable damping. Particular means for mounting and wiring crystal oscillators are described in co-pending application Ser. No. 07/290,533, the disclosure of which is incorporated herein by reference.

The present invention, however, is not limited to the use of piezoelectric crystal oscillators as the ultrasonic transducer, and organic electsets such as polyvinylidene difluoride (PVDF) and vinylidene fluoridetrifluoroethylene copolymers may also find use. PVDF is particularly suitable as a transducer at higher frequencies, typically at or above about 40 MHz.

The ultrasonic transducers of the present invention will be connected to conventional transmitting and receiving units which include the circuitry necessary for interpreting the ultrasonic information and displaying such information on a visual display, such as a cathode ray tube. Normally, the transmitter receiver unit will operate in a pulse-echo mode which penetrates the stenosis and blood vessel surrounding the distal end of the catheter to provide a profile including the inner face between the stenosis and the blood vessel wall.

Suitable lasers which may be connected to the catheter of the present invention include those lasers having sufficiently high power densities to effect ablation of the stenosis. Suitable lasers include neodymium-YAG (yttrium-aluminum-garnate), ruby rod, argon, and excimer (pulsed dye) lasers. A thorough discussion of the attachment of lasers to vascular catheters is provided in U.S. Pat. No. 4,576,177, the disclosure of which is incorporated herein by reference.

Laser energy will be delivered through the catheter of the present invention by optical waveguides. The waveguides will usually be formed from fused silica or quartz glass, and may include one fiber or a bundle of fibers. Typically, the waveguides will be arranged in a bundle having a circular cross-section with a diameter in the range from about 0.1 to 1 mm, but have a variety of other geometries depending on the particular application. Various lenses may be provided at the distal end of the optical waveguides to provide for dispersion or focusing of the laser radiation. The specific embodiments described hereinafter will not include such lenses, but it will be appreciated that they could be incorporated without any appreciable modification of the designs.

A rotatable reflective element will be provided for scanning the ultrasonic imaging signal (and optionally the laser energy) across the interior of the, blood vessel. Typically, imaging will be performed at a relative high scan rate in the range from 100 to 20,000 rpm, usually being in the range from 500 to 2,000 rpm, with the rotatable element being connected to a motor drive unit. Scanning at lower speeds and manual scanning will also be possible. Both image scanning and laser ablation, of course, may be performed during only a portion of the rotation of the reflective element. Moreover, the element may be oscillated through an angle less than 360° rather than being fully rotated.

Referring now to FIG. 1, a catheter 10 constructed in accordance with the principles of the present invention comprises an elongate flexible catheter tube 12 formed from a suitable material, such as a suitable thermoplastic or thermosetting plastic. A housing 14 is mounted at a distal end of flexible catheter tube 12 and includes a generally open volume 16 therein. As illustrated, the housing 14 is formed separately from the flexible catheter tube 12. The present invention, however, contemplates that the housing 14, or portions thereof, may be formed integrally with the flexible catheter tube 12.

Rotatable member 18 is mounted within the open volume 16 of housing 14 on a rotatable cable 20. Cable 20 extends axially through a fiber optic bundle 22 which terminates just behind (i.e., to the right in FIG. 1) rotatable element 18. An ultrasonic transducer 24 is mounted to circumscribe the fiber optic bundle 22 proximate its termination point.

Rotatable element 18 includes a reflective surface 26 disposed toward the fiber optic bundle 22 and ultrasonic transducer 24. The rotatable element 18 is shaped as a truncated cylinder so that surface 26 has an elliptical periphery. The plane of surface 26 is inclined relative to the axis of housing 14, while the fiber optic bundle is generally aligned coaxially with the axis. The ultrasonic transducer is generally aligned coaxially, while the fiber optic bundle is generally aligned coaxially with the axis. The ultrasonic transducer 24 is arranged to transmit and receive ultrasonic energy in a direction generally parallel with the axis of housing 14 by inclining the reflective surface at a 45° angle relative to the axial direction, both the ultrasonic signal generated by transducer 24 and laser energy transmitted by fiber optic bundle 22 are reflected in a transverse or longitudinal direction as indicated by broken lines 30 and 32, respectively.

A proximal housing 36 is connected at the proximal end of flexible catheter tube 12. Both the cable 20 and the fiber optic bundle 22 extend from the distal end of the catheter through lumen 13 and enter into interior chamber 38 formed within the proximal housing 36. A pair of wires 40 also extend through lumen 13 from the ultrasonic transducer 24 to a fitting 42 formed on the side of the proximal housing 36. The fitting 42 is suitable for connection to an external ultrasonic transmitter and receiver unit for performing the imaging functions in a conventional manner.

Fiber optic bundle 20 is taken out of housing 36 through a second fitting 44, and a third fitting 43 is provided for supplying a suitable liquid filler for the catheter.

The rotatable cable 20 extends axially through the housing 36 and out through an O-ring chamber 46 formed at the distal end. A drive shank 48 is coupled to the end of cable 20 and allows for attachment to an external rotating drive means. A suitable system for rotating the rotatable element 18 for use in imaging according to the present invention is described in U.S. Pat. No. 4,794,931, which has previously been incorporated herein by reference.

A flexible guidewire 50 may be attached to the forward distal end of housing 14, as illustrated in FIG. 1. The guidewire is useful for allowing the catheter 10 to be advanced through the vascular system to the region of stenosis. Alternatively, the catheter 10 could be adapted to accept a separate guidewire which is inserted prior to insertion of the catheter. To allow for such a guidewire, the cable 20 would have to be hollow with axial openings provided in both the rotatable member 18 and forward end of housing 14.

Referring now to FIG. 3, an image 56 of the type provided by catheter 10 is illustrated. The image provides a profile 58 of the catheter 10 as well as the interior surface 60 of the material occluding the blood vessel. Importantly, the profile image 56 also includes the outline of the interface between the stenosis material and the blood vessel wall 62. Thus, the image provides sufficient information to determine the depth of the stenosis material in all directions surrounding the catheter. The image also provides information concerning the density and hardness of the stenosis material so that the user can determine how much energy is appropriate to remove the material without penetrating into the healthy blood vessel wall.

Once the image profile of the blood vessel and the region of stenosis is obtained, the user can decide where to direct the laser energy by properly positioning the rotatable element 18. The laser can then be directed to the stenosis material in discrete bursts, or by sweeping the beam back and forth across a particular region. By virtue of employing a coaxial ultrasonic scan beam and laser beam, the stenosis can be imaged synchronously and simultaneously with the on-going process.

Referring now to FIGS. 4 and 5, the second embodiment of the catheter of the present invention will be described. The catheter 100 comprises an elongate flexible catheter tube 102 having a central lumen 104. The composition and dimensions of the flexible catheter tube will be similar to those described for the embodiments of FIG. 1 and 2, except that a second lumen 106 will be provided to accommodate optical waveguide 108. The optical waveguide 108 terminates at the distal end of the flexible catheter tube 102 so that it is able to direct laser energy forward in an axial path which is parallel to but spaced-apart from the central axis of the tube.

A housing 110 is attached to the forward distal end of the flexible catheter tube 102 and includes a cutout 112. The housing 110 may be formed from any suitable material, including both biologically compatible metals and plastics, and the cutout 112 provides an unimpeded port for directing laser energy outwardly, as will be described in greater detail hereinafter.

Rotatable element 116 is mounted within the interior of housing 110 and attached to the forward end of rotatable cable 118. The rotatable element 116 includes a first reflective surface 120 which is provided to transversely deflect an ultrasonic scanning signal and a second reflective surface 122 which is provided to transversely deflect the laser energy emanating from optical waveguide 108. An ultrasonic transducer 124 is provided in the tip of the housing 110 and disposed to project an ultrasonic beam in the generally rearward (to the right in FIG. 4) direction. Broken lines 126 generally indicate the transverse reflection provided by the first reflective surface 120. The radial direction of the reflected beams can be changed by rotating the rotatable element 116 by in turn rotating the cable 118.

The direction of laser energy emanating from optical waveguide 108 is indicated by broken line 128. The precise direction that the laser beam is deflected is controlled by the angle of the second reflective surface 122. As can be seen, the laser beam intersects the path of the ultrasonic transducer signal. Moreover, the radial direction of the laser beam will synchronously track the radial direction of the ultrasonic transducer beam so that the effect of the laser energy on the stenosis can be observed substantially in real time.

The rotatable element 116 can be axially advanced and retracted by properly positioning the cable 118. This is an advantage as it allows ultrasonic scanning of a discrete length of the blood vessel prior to any treatment with laser energy. Thus, a great deal of information concerning the stenosis can be obtained prior to any treatment without any movement of the catheter as a whole. The catheter is then able to provide a fixed reference frame in performing the laser treatment. This is more difficult to achieve with catheters which must be advanced and retracted as a whole within the blood vessel.

Catheter 100 includes a central bore 130 formed through the tip of housing 110. A hole 132 aligned with bore 130 is formed in the ultrasonic transducer 124, and a lumen 134 is formed through the drive cable 118. In this way, the catheter 100 is adapted to be inserted into a patient's vascular system over a conventional guidewire. The catheter 100 could alternately be formed with a fixed guidewire, as illustrated with the catheter of FIGS. 1 and 2. The catheter 100 will also include a proximal housing (not illustrated) at the proximal end of flexible catheter tube 102. The housing will be similar to housing 36 illustrated in FIG. 1, except that the housing will be adapted to allow forward and rearward motion of the drive cable 118 to allow axial positioning of the rotatable element 116. The constructions of housings with this capability is illustrated in co-pending application Ser. No. 07/290,533, the disclosure of which has previously been incorporated herein by reference.

Referring now to FIG. 6, a third embodiment of a catheter constructed in accordance with the principles of the present invention is illustrated. The catheter 150 again includes a flexible catheter tube 152, a rotatable drive cable 154 extending from a proximal end (not shown) of the flexible tube to the distal end through a lumen 156, and a housing 158 formed at the distal end of the tube. An optical waveguide 160 extends from the proximal end of the tube 152, through the housing 158, and terminates at the forward end of the housing (to the left as illustrated in FIG. 6). The optical waveguide 156 is adapted to project laser energy in a generally axially forward direction from the catheter 150, and may include lenses, optical grates, or the like as desired to focus or disperse the laser energy.

A mechanism (not illustrated) may be provided for transversely deflecting the tip of catheter 150 in order to allow aiming of the laser energy emanating from waveguide 160. For example, an offset cable running the length of flexible catheter tube 150 would provided deflection by applying tension to the tip. Alternatively, inflatable balloons asymmetrically mounted on the tip could provide for deflection mechanisms for catheter tip deflection are described in U.S. Pat. No. 4,418,688, the disclosure of which is incorporated herein by reference.

An ultrasonic transducer 162 is provided at the forward end of an internal cavity 164 within the housing 158. Transducer 162 directs ultrasonic energy rearward toward rotatable element 166 which is mounted on the forward end of drive cable 154. The ultrasonic energy reflects against reflective surface 168 on the forward end of rotatable element 166, so that the energy may be swept in a generally conical pattern as illustrated by broken lines 170. The reflective surface 168, of course, can also receive echo pulses from the ultrasonic energy, in turn reflecting them back to the transducer 162 which can feed the information to a suitable transmitter/receiver unit, as discussed previously. Optionally, the rotatable element 166 may be axially translatable by moving the drive cable 154 forward and rearward in a conventional manner. Catheter 150 is useful to provide for proper centering of laser energy provided by the optical waveguide 160 down the central part of the blood vessel lumen.

As illustrated in FIG. 6, waveguide 160 is radically offset from the axis of lumen 156. Such design allows use of a solid core cable 154 and avoids the need to penetrate the mirror 166, transducer 162, and distal tip of the catheter. It also results in the waveguide 160 being aimed away from the center of the field of view of the catheter. In some causes it will be desirable to extend the wave guide down the center axis of the catheter 150. This can be accomplished by making cable 154 hollow and penetrating the mirror 166, transducer 162, and catheter tip.

Referring now to FIGS. 7-9, a fourth embodiment of the catheter of the present invention is intended for incrementally removing or shaving layers of stenosis from the inner periphery of a blood vessel lumen. The catheter 200 again includes flexible catheter tube 202, a rotatable drive cable 204 extending from a proximal end of the tube (not illustrated) to a distal end through lumen 206, and a housing 208 attached to the distal end of the tube. An optical waveguide 210 extends through a second lumen in the flexible tube 202, through the lumen in the housing 208, and terminates at a point midway along the periphery of the housing, as illustrated. An inflatable balloon 212 is formed on the housing 208 on a side substantially opposite from the optical waveguide 210. A third lumen 214 within the flexible catheter tube 202 provides inflation medium for the balloon 212, in a conventional manner.

A rotatable element 214 is mounted within open cylindrical chamber 216 formed within the housing 208. An ultrasonic transducer 218 is mounted on the forward end of chamber 216 and disposed to direct an ultrasonic signal in the generally rearward (to the right in FIG. 7) direction. Rotatable element 214 includes a forward reflective surface 220 which is disposed to transversely deflect the ultrasonic signal emanating from transducer 218, as illustrated by lines 222. In this way, the catheter 200 can provide radial scan information substantially similar to that illustrated in FIG. 3 discussed above.

Based on this information, catheter 200 can be rotated within the blood vessel so that the termination point of waveguide 210 is generally radially aligned with the portion of atheroma or plaque which is desired to be removed. The optical waveguide can be urged against the plaque by inflation of balloon 212 so that the plaque will lie substantially forward of the optical waveguide 210. Then, by providing controlled pulses or bursts of laser energy, the atheroma can be incrementally ablated. The length of the pulse and/or the number of pulses can be controlled to obtain a desired ablation rate. The total amount of material removed can be visually controlled by the user.

Use of catheter 200 contemplates that the catheter will be manipulated within the blood vessel to incrementally remove relatively large portions of the material obstructing the blood vessel. As the laser radiation is directed substantially axially, however, the danger of penetrating the blood vessel wall is greatly diminished. Moreover, this embodiment allows for widening of the vessel lumen in contrast to most prior art laser catheters which are intended for penetrating the central lumen.

A modification of the optical waveguide 210' is illustrated in FIG. 9. There, the waveguide terminates in a crescent-shaped annular section which extends over a portion of the periphery of housing 208. In this way, annular layers of plaque can be removed, rather than relatively narrow paths.

Although the foregoing invention has been described in some detail by way of illustration and example for purposes of clarity of understanding, it will be obvious that certain changes and modifications may be practiced within the scope of the appended claims.

What is claimed is:

1. A vascular catheter comprising:
   a flexible tube having proximal and distal ends, said distal end defining a longitudinal axis;
   a rotatable member having a first reflective surface and a second reflective surface, said surfaces being oriented transversely to the longitudinal axis;
   means for rotating the rotatable member about the longitudinal axis;
   an ultrasonic transducer mounted within the distal end of the flexible tube, said transducer being disposed to direct ultrasonic energy against the first reflective surface whereby a preselected path can be ultrasonically scanned; and
   an optical waveguide disposed to direct laser radiation against the second reflective surface, wherein said first and second reflective surfaces are relatively oriented so that reflected laser radiation will intersect the ultrasonic scan path at a preselected location outside of the distal end of the flexible tube, whereby rotation of the rotatable member synchronously rotates the ultrasonic energy and the laser radiation.

2. A vascular catheter comprising:
   a flexible tube having proximal and distal ends, said distal end defining a longitudinal axis;
   a rotatable member having a reflective surface oriented transversely to the longitudinal axis;
   means for rotating the rotatable member about the longitudinal axis;
   an ultrasonic transducer mounted within the distal end of the flexible tube, said transducer being disposed to direct ultrasonic energy against the reflective surface whereby a preselected path can be ultrasonically scanned;
   an optical waveguide capable of directing laser radiation along a generally longitudinal path which intersects the ultrasonic scan path at a preselected location outside of the distal end of the flexible tube; and
   an inflatable balloon on the periphery of the flexible tube at a location opposite the optical waveguide termination.

3. A vascular catheter as in claim 2, wherein the reflective surface is oriented to provide a transverse planar ultrasonic scan path.

4. A vascular catheter as in claim 2, wherein the optical waveguide terminates on the periphery of the flexible tube at a location substantially within the ultrasonic scan path.

* * * * *